(12) United States Patent
Seo et al.

(10) Patent No.: US 9,203,012 B2
(45) Date of Patent: Dec. 1, 2015

(54) ULTRASOUND PROBE AND MANUFACTURING METHOD THEREOF

(71) Applicant: SAMSUNG MEDISON CO., LTD., Gangwon-do (KR)

(72) Inventors: Min Seon Seo, Gyeongju-si (KR); Ji Seon Kim, Daegu (KR); Sung Jae Lee, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 389 days.

(21) Appl. No.: 13/732,015

(22) Filed: Dec. 31, 2012

(65) Prior Publication Data

US 2013/0169112 A1  Jul. 4, 2013

(30) Foreign Application Priority Data

Jan. 2, 2012  (KR) .................. 10-2012-0000105

(51) Int. Cl.
| | | |
|---|---|---|
| H01L 41/047 | (2006.01) | |
| H01L 41/08 | (2006.01) | |
| B06B 1/06 | (2006.01) | |
| H01L 41/04 | (2006.01) | |
| H01L 41/25 | (2013.01) | |
| A61B 8/00 | (2006.01) | |

(52) U.S. Cl.
CPC .......... *H01L 41/0825* (2013.01); *A61B 8/4494* (2013.01); *B06B 1/0629* (2013.01); *H01L 41/04* (2013.01); *H01L 41/25* (2013.01); *B06B 1/064* (2013.01); *Y10T 29/42* (2015.01)

(58) Field of Classification Search
CPC ....................................................... H04R 17/00
USPC ......... 310/320–322, 326, 327, 334, 365, 366; 29/25.35
See application file for complete search history.

(56) References Cited

U.S. PATENT DOCUMENTS

| | | | |
|---|---|---|---|
| 5,553,035 A * | 9/1996 | Seyed-Bolorforosh et al. ............... | 367/140 |
| 5,630,837 A * | 5/1997 | Crowley ........................... | 601/2 |
| 6,236,144 B1 * | 5/2001 | Millar et al. .................. | 310/334 |
| 6,415,507 B1 * | 7/2002 | Shimosato et al. .......... | 29/890.1 |
| 6,856,579 B1 * | 2/2005 | Benjamin et al. ............. | 367/154 |
| 2002/0156373 A1 * | 10/2002 | Wakabayashi et al. ....... | 600/437 |
| 2003/0055337 A1 * | 3/2003 | Lin ............................... | 600/459 |
| 2008/0200812 A1 * | 8/2008 | Osawa .......................... | 600/459 |

FOREIGN PATENT DOCUMENTS

| | | |
|---|---|---|
| KR | 2010-0104535 A | 9/2010 |
| KR | 20110047019 A | 5/2011 |

OTHER PUBLICATIONS

Korean Office Action issued in Korean Application No. 10-2012-0000105 mailed Jun. 27, 2013.

* cited by examiner

*Primary Examiner* — Thomas Dougherty
(74) *Attorney, Agent, or Firm* — McDermott Will & Emery LLP

(57) ABSTRACT

An ultrasound probe including a backing layer provided with grooves in which a piezoelectric member is allowed to be installed and a manufacturing method thereof. The ultrasound probe includes the piezoelectric member, and the backing layer disposed on a rear-side surface of the piezoelectric member and provided, on a front-side surface thereof, with grooves in which the piezoelectric member is installed.

27 Claims, 17 Drawing Sheets

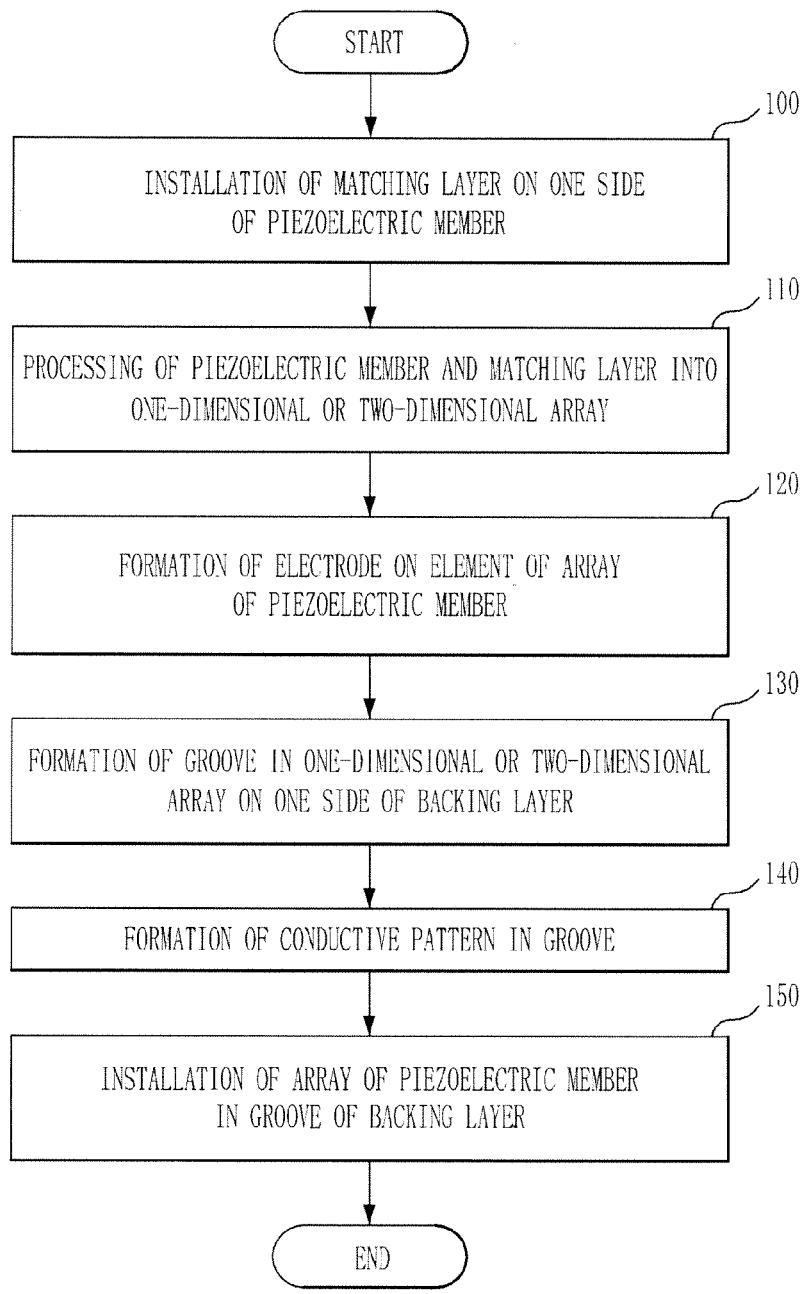

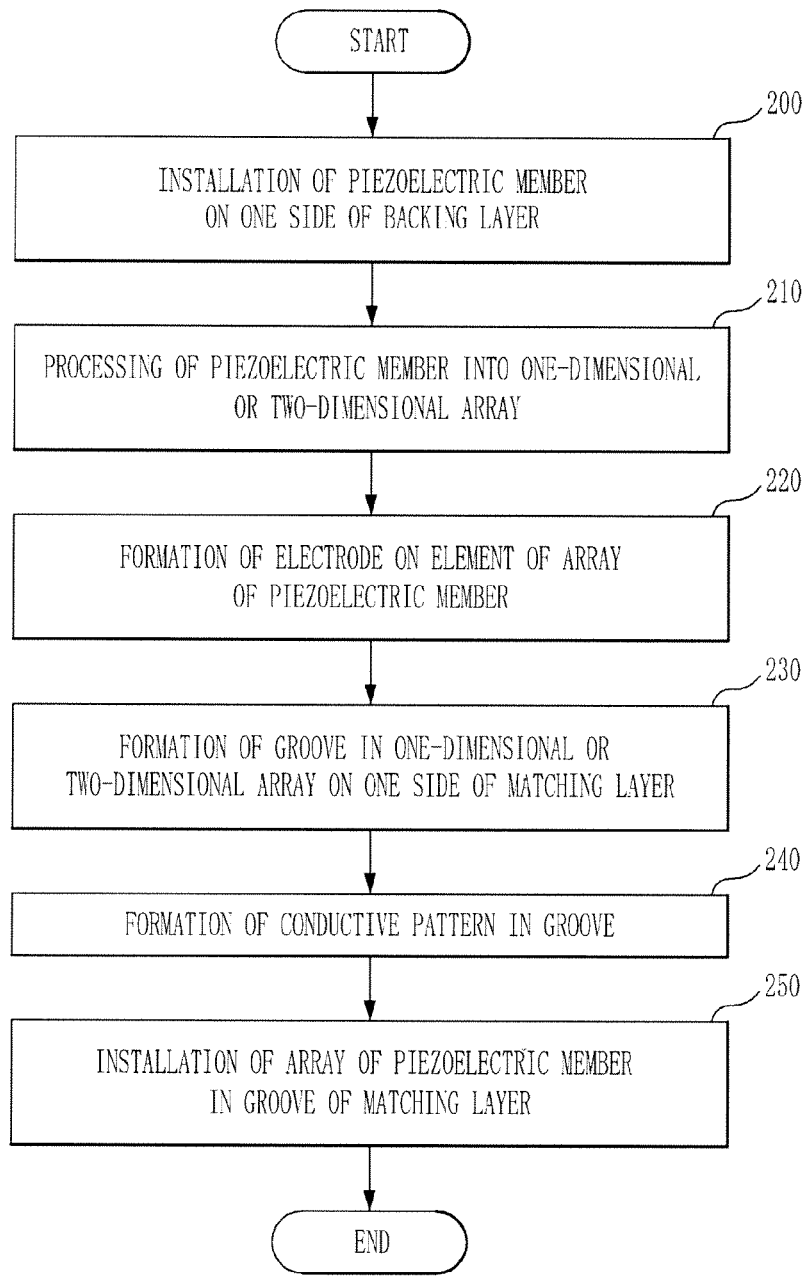

ULTRASOUND PROBE AND MANUFACTURING METHOD THEREOF

CROSS-REFERENCE TO RELATED APPLICATION

This application claims the benefit of Korean Patent Application No. 10-2012-0000105, filed on Jan. 2, 2012 in the Korean Intellectual Property Office, the disclosure of which is incorporated herein by reference.

BACKGROUND

1. Field

Exemplary embodiments of the present disclosure relate to an ultrasound probe for generating images of the inside of a subject using ultrasonic waves.

2. Description of the Related Art

An ultrasound diagnostic system includes a noninvasive apparatus that irradiates an ultrasound signal to a body surface at a target organ in the body and obtains cross-sectional images of, for example, soft tissue and blood flow.

Compared to other imaging diagnostic systems such as X-ray diagnostic systems, computed tomography (CT) scanners, magnetic resonance imaging (MRI) systems and diagnostic systems for nuclear medicine, the ultrasound diagnostic system may have a compact size and low price, display images in real time, and provide a high level of safety by eliminating exposure to radiation. For at least these reasons, an ultrasound diagnostic system has been widely used for diagnosis in, for example, cardiac medicine, abdominal imaging, urology, obstetrics and gynecology.

The ultrasound diagnostic system includes an ultrasound probe which transmits an ultrasound signal to a subject and receives an ultrasound echo signal reflected from the subject to obtain an ultrasound image of the subject.

The ultrasound probe includes a piezoelectric layer of piezoelectric materials which convert electric signals into sound signals (e.g., acoustic), and vice versa, through vibration of the piezoelectric materials, a matching layer to reduce a difference in acoustic impedance between the piezoelectric layer and the subject to allow ultrasonic waves transmitted from the piezoelectric layer to be transferred to the subject as much as possible, and a lens to focus the ultrasonic waves traveling from the front of the piezoelectric layer on a specific point, and a backing layer to block the ultrasonic waves from traveling in an opposite direction from the rear of the piezoelectric layer to prevent image distortion.

SUMMARY

Therefore, it is an object of the present disclosure to provide an ultrasound probe including a backing layer and/or a matching layer provided with grooves in which a piezoelectric member is allowed to be installed, and a manufacturing method thereof.

Additional objects of the present disclosure will be set forth in part in the description which follows and, in part, will be obvious from the description, or may be learned from practice of exemplary embodiments of the present disclosure.

In accordance with one aspect of the present disclosure, an ultrasound probe includes a piezoelectric member, and a backing layer disposed on a rear-side surface of the piezoelectric member and provided, on a front-side surface of the backing layer, with at least one groove in which the piezoelectric member is installed.

The piezoelectric member may be arranged as one of a one-dimensional array and a two-dimensional array, and the at least one groove may have a shape corresponding to the array of the piezoelectric member.

A ground electrode may be formed on at least one side of each of elements constituting the array of the piezoelectric member, and a signal electrode may be formed on at least one side of each of the elements including a side opposite to the side on which the ground electrode is formed.

At least one conductive pattern to apply an electric signal to the array of the piezoelectric member may be installed in the at least one groove.

The at least one conductive pattern may be formed on at least one side of the at least one groove.

The at least one conductive pattern may be electrically connected with at least one of a ground electrode and a signal electrode formed on an element of the array of the piezoelectric member to apply an electric signal to the element.

In accordance with another aspect of the present disclosure, an ultrasound probe includes a piezoelectric member, and a matching layer disposed on a front-side surface of the piezoelectric member and provided, on a rear-side surface of the matching layer, with at least one groove in which the piezoelectric member is installed.

The piezoelectric member may be arranged as one of a one-dimensional array and a two-dimensional array, and the at least one groove may have a shape corresponding to the array of the piezoelectric member.

A ground electrode may be formed on at least one side of each of elements constituting the array of the piezoelectric member, and a signal electrode may be formed on at least one side of each of the elements including a side opposite to the side on which the ground electrode is formed.

At least one conductive pattern to apply an electric signal to the array of the piezoelectric member may be installed in the at least one groove.

The at least one conductive pattern may be formed on at least one side of the at least one groove.

The at least one conductive pattern may be electrically connected with at least one of a ground electrode and a signal electrode formed on an element of the array of the piezoelectric member to apply an electric signal to the element.

In accordance with one aspect of the present disclosure, a manufacturing method of an ultrasound probe includes forming at least one groove on one side of a backing layer, and installing a piezoelectric member in the at least one groove.

The forming at least one groove may include arranging, on the one side of the backing layer, the at least one groove in one of a one-dimensional array and a two-dimensional array, and forming, on at least one side of the at least one groove, at least one conductive pattern to apply an electric signal to the array of the piezoelectric member.

The installing a piezoelectric member may include installing a matching layer on one side of the piezoelectric member, processing the piezoelectric member on which the matching layer is installed into one of a one-dimensional array and a two-dimensional array, forming a ground electrode and a signal electrode on each of elements constituting the array of the processed piezoelectric member, and installing, in the at least one groove, the array of the piezoelectric member provided with the ground and signal electrodes.

The forming a ground electrode and a signal electrode may include forming the ground electrode on at least one side of each element constituting the array of the processed piezoelectric member, and forming the signal electrode on at least one side of each element including a side opposite to the side on which the ground electrode is formed.

At least one conductive pattern may be formed in the at least one groove to be electrically connected with at least one of the ground electrode and the signal electrode to apply an electric signal to the element.

In accordance with another aspect of the present disclosure, a manufacturing method of an ultrasound probe includes forming at least one groove on one side of a matching layer, and installing a piezoelectric member in the at least one groove.

The forming at least one groove may include arranging, on the one side of the matching layer, the at least one groove in one of a one-dimensional array and a two-dimensional array, and forming, on at least one side of the at least one groove, at least one conductive pattern to apply an electric signal to the array of the piezoelectric member.

The installing a piezoelectric member may include processing the piezoelectric member into one of a one-dimensional array and a two-dimensional array, forming a ground electrode and a signal electrode on each of elements constituting the array of the processed piezoelectric member, and installing, in the at least one groove, the array of the piezoelectric member provided with the ground and signal electrodes.

The forming a ground electrode and a signal electrode may include forming the ground electrode on at least one side of each element constituting the array of the processed piezoelectric member, and forming the signal electrode on at least one side of each element including a side opposite to the side on which the ground electrode is formed.

At least one conductive pattern may be formed in the at least one groove to be electrically connected with at least one of the ground electrode and the signal electrode to apply an electric signal to the element.

In accordance with another aspect of the present disclosure, an ultrasound probe includes a piezoelectric member including a front-side surface and a rear-side surface, a backing layer disposed on the rear-side surface for absorbing at least a portion of ultrasonic waves generated in the piezoelectric member, and a matching layer disposed on the front-side surface for reducing a difference in acoustic impedance between the piezoelectric member and a subject, wherein at least one of the backing layer and matching layer includes a groove in which the piezoelectric member is installed.

The backing layer may include the groove.

The matching layer may include the groove.

A conductive pattern may be formed in the groove to apply an electric signal to the piezoelectric member.

An electrode may be formed on a surface of the piezoelectric member and electrically coupled to the conductive pattern.

BRIEF DESCRIPTION OF THE DRAWINGS

These and/or other aspects of the present disclosure will become apparent and more readily appreciated from the following description of the embodiments, taken in conjunction with the accompanying drawings of which:

FIG. 16 is a flowchart illustrating a manufacturing method of the ultrasound probe according to an exemplary embodiment of the present disclosure;

FIG. 17 is a flowchart illustrating a manufacturing method of the ultrasound probe according to the another embodiment of the present disclosure.

DETAILED DESCRIPTION

Figure 1:
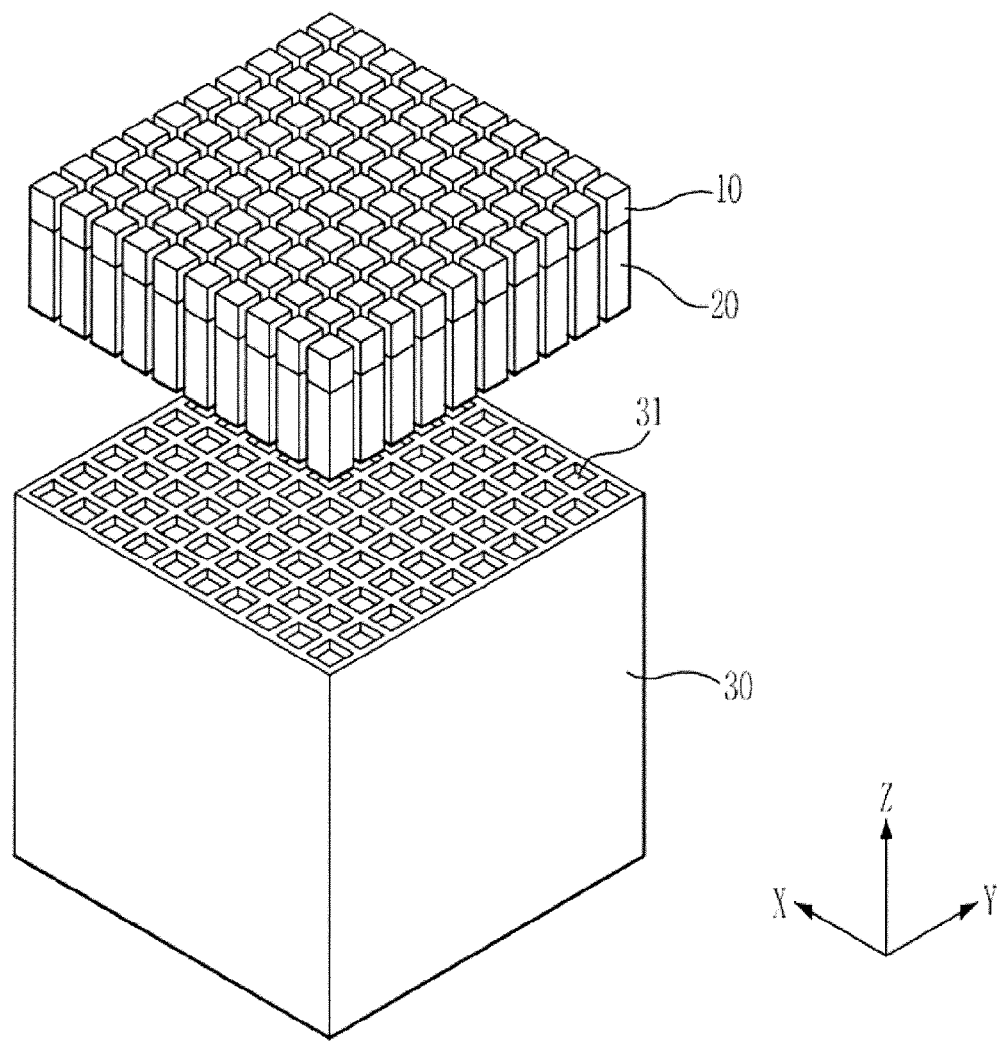
FIGS. 1 and 2 are exploded perspective views illustrating an ultrasound probe according to an exemplary embodiment of the present disclosure.

Reference will now be made in detail to exemplary embodiments of the present disclosure, examples of which are illustrated in the accompanying drawings, wherein like reference numerals refer to like elements throughout.

Figure 2:
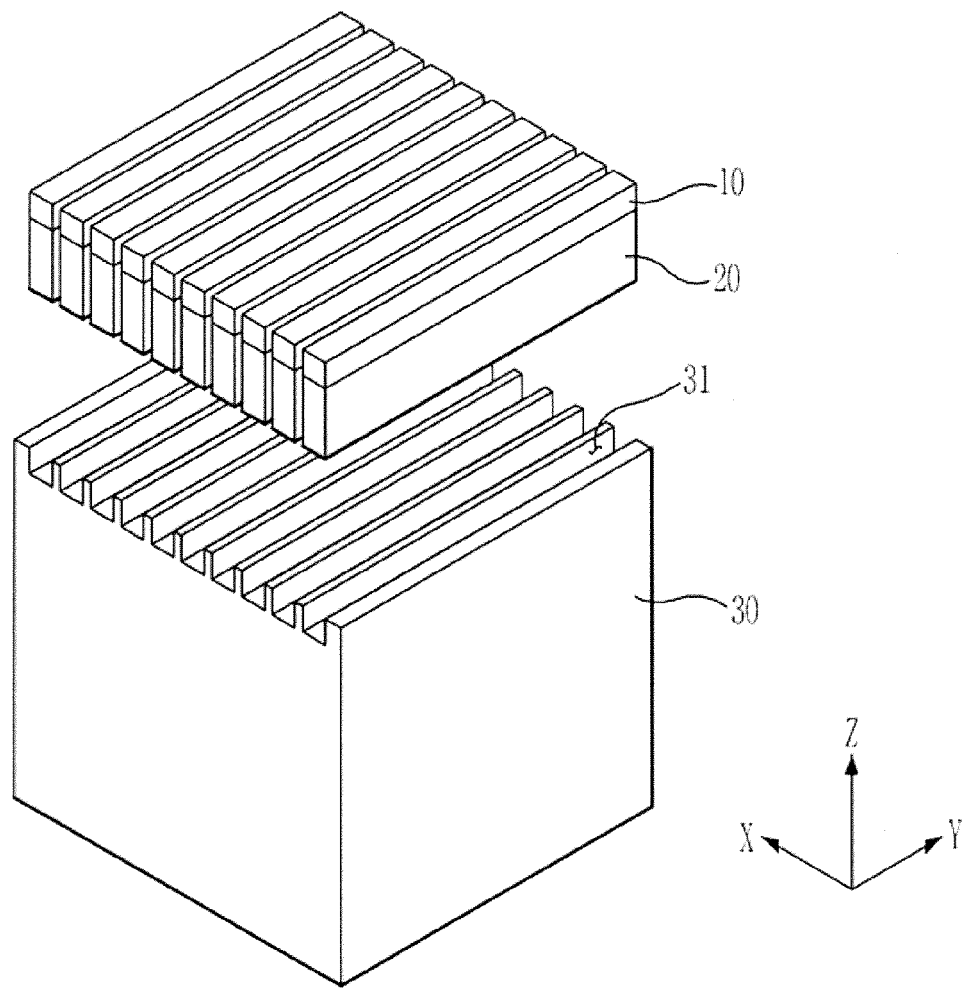

FIG. 1 is an exploded perspective view illustrating a two-dimensional-array of an ultrasound probe according to an exemplary embodiment of the present disclosure, and FIG. 2 is an exploded perspective view illustrating a one-dimensional-array of an ultrasound probe according to an exemplary embodiment of the present disclosure.

The ultrasound probe according to the exemplary embodiment includes a piezoelectric layer 20, a matching layer 10 disposed on a front-side surface of the piezoelectric layer 20, and a backing layer 30 disposed on a rear-side surface of the piezoelectric layer 20.

A piezoelectric material generates a voltage in response to applied mechanical stress, and is mechanically deformed in response to an applied voltage. These effects are referred to as a piezoelectric effect and an inverse piezoelectric effect, respectively.

That is, a piezoelectric material is a material that converts electric energy into mechanical vibration energy, and vice versa.

The ultrasound probe according to an exemplary embodiment includes the piezoelectric layer 20 formed of a piezoelectric material(s) that generates an ultrasound by converting an applied electric signal into mechanical vibration.

Examples of piezoelectric materials constituting the piezoelectric layer 20 may include at least one of lead zirconate titanate (PZT) ceramics, PZMT single crystals made of a solid solution of lead magnesium niobate and lead titanate, PZNT single crystals made of a solid solution of lead zinc niobate and lead titanate, or the like.

In addition, the piezoelectric layer 20 may be arranged in either a single layer or a multilayered stack.

In general, when the piezoelectric layer 20 is arranged in a multilayered stack, the impedance and voltage of the piezoelectric layer 20 may be adjusted more easily, and better piezoelectric sensitivity, higher energy conversion efficiency and a smoother spectrum may be obtained.

The matching layer 10 is disposed on the front-side surface of the piezoelectric layer 20. The matching layer 10 reduces a difference in acoustic impedance between the piezoelectric layer 20 and the subject to enable matching the acoustic impedance of the piezoelectric layer 20 with that of the subject, thereby allowing ultrasound generated by the piezoelectric layer 20 to be efficiently transferred to the subject.

To this end, the matching layer 10 may be adapted to have a middle value between the acoustic impedances of the piezoelectric layer 20 and the subject.

The matching layer 10 may be formed of a glass or resin material. Also, a plurality of matching layers 10 may be provided to allow the acoustic impedance to vary gradually from the piezoelectric layer 20 toward the subject, and each of the plurality of matching layers may be formed of a different material.

The piezoelectric layer 20 and the matching layer 10 may be formed in a dicing process as a two-dimensional array in the shape of a matrix shown in FIG. 1, or as a one-dimensional array shown in FIG. 2.

Although not shown in FIGS. 1 and 2, a protective layer may be disposed on a front-side surface of the matching layer 10. The protective layer may prevent high frequency signals generated by the piezoelectric layer 20 from being exposed to the outside and may block introduction of external high frequency signals.

Further, the protective layer may protect internal components from water and chemicals such as those used for disinfection, by applying or depositing a conductive material to the surface of a film with moisture-resistance and chemical resistance.

Although not shown in FIGS. 1 and 2, a lens may be disposed on the front-side surface of the matching layer 10. The lens may be formed to be convex in a direction of irradiation of the ultrasonic waves to focus the ultrasonic waves, or may be formed to be concave in case the sound velocity is lower than in the subject.

The backing layer 30, which is disposed on the rear-side surface of the piezoelectric layer 20, absorbs a portion of the ultrasonic waves generated in the piezoelectric layer 20 and traveling in a backward direction. This blocks the portion of the ultrasonic waves from being reflected in a forward direction, thereby preventing image distortion. To enhance attenuation or blocking of ultrasound, a plurality of backing layers 30 may be provided.

When the piezoelectric layer 20 is formed as a two-dimensional array, the backing layer 30 is also formed to have a plurality of grooves 31 arranged in a two-dimensional array, as shown in FIG. 1.

The number of grooves 31 may be equal to that of elements 21 (see FIG. 4) constituting the two-dimensional array of the piezoelectric layer 20, and each of the grooves 31 may be formed to have the same or a similar cross-sectional shape as that of the corresponding element 21 so that the respective elements 21 may be seated in the grooves 31.

When the piezoelectric layer 20 is formed as a one-dimensional array, the backing layer 30 is also formed to have a plurality of grooves 31 arranged in a one-dimensional array, as shown in FIG. 2.

The number of grooves 31 may be equal to that of elements 21 constituting the one-dimensional array of the piezoelectric layer 20, and each of the grooves 31 may be formed to have the same or a similar cross-sectional shape as that of the corresponding element 21 so that the respective elements 21 may be seated in the grooves 31.

The depth of the grooves 31 may be set to allow the elements 21 to be stably seated while not degrading the efficiency of generating ultrasonic waves.

The manufacturing technique used for forming the grooves 31 in the backing layer 30 is not limited. Various manufacturing techniques may be used depending on, for example, the shape of the grooves 31. For instance, in one exemplary process, the backing layer 30 provided with grooves 31 may be manufactured through casting.

When the elements 21 are installed in corresponding grooves 31, an adhesive, a silver epoxy, a conductive material, or the like, may be inserted between contact surfaces of the element 21 and the groove 31 for increasing accuracy in arranging the elements 21 to allow the elements 21 to be securely installed in the grooves 31.

Figure 3:
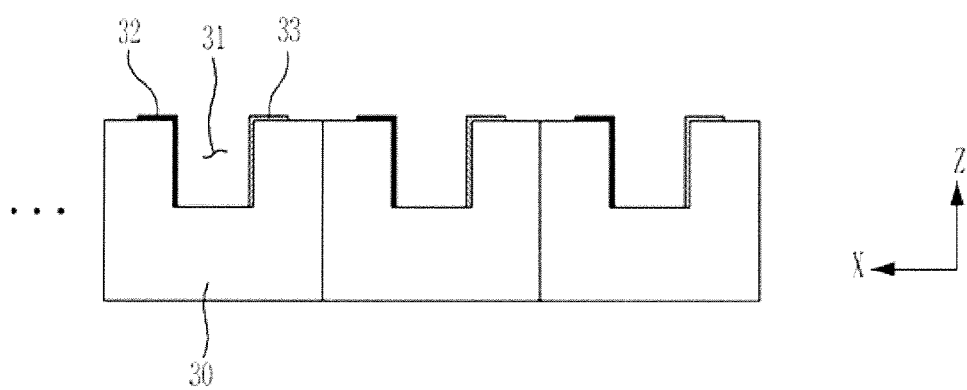
FIG. 3 is a view illustrating an example of formation of conductive patterns in grooves of a backing layer of the ultrasound probe according to an embodiment of the present disclosure.
Figure 4:
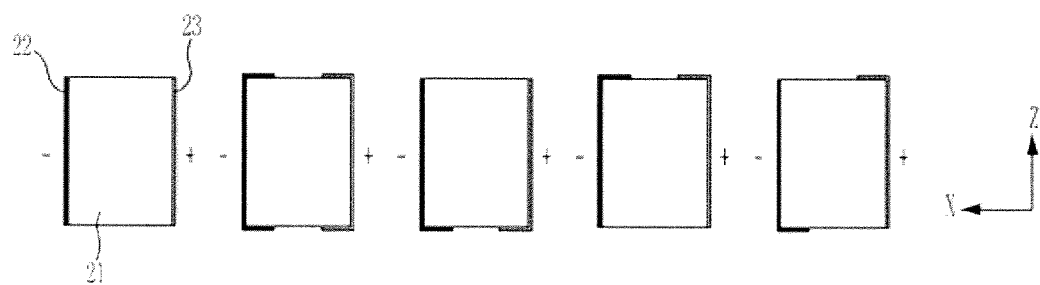
FIG. 4 is a view illustrating an example of a piezoelectric member provided with electrodes to be installed in the grooves of FIG. 3.
Figure 5:
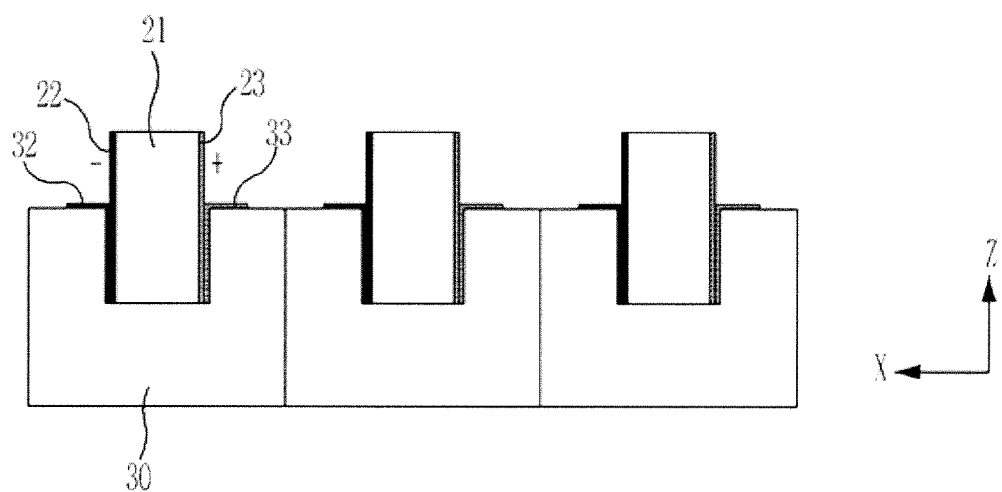
FIG. 5 is a view illustrating installation of the piezoelectric member of FIG. 4 in the grooves of FIG. 3.
Figure 6:
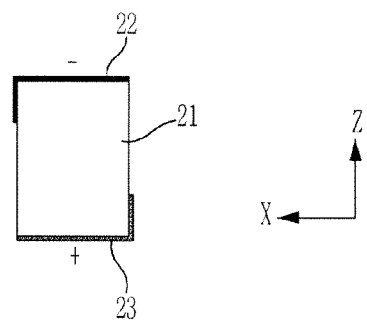
FIG. 6 is a view illustrating another example of the piezoelectric member provided with electrodes to be installed in the grooves of FIG. 3.
Figure 7:
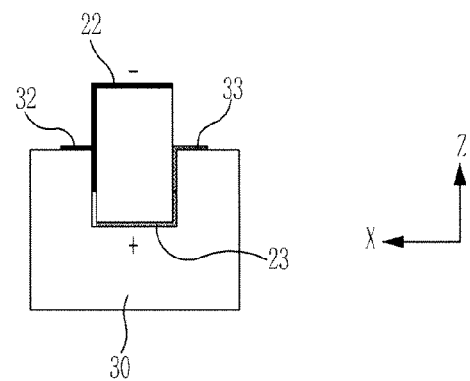
FIG. 7 is a view illustrating installation of the piezoelectric member of FIG. 6 in the grooves of FIG. 3.

FIG. 3 illustrates an example of conductive patterns 32 and 33 formed in the grooves 31 of the backing layer 30 of the ultrasound probe according to an exemplary embodiment of the present disclosure, FIGS. 4 and 5 illustrate an example of a piezoelectric member which may be installed in the groove 31 in FIG. 3 and installation thereof in the groove 31, respectively, and FIGS. 6 and 7 illustrate another example of a piezoelectric member which may be installed in the groove 31 in FIG. 3 and installation thereof in the groove 31, respectively.

For the piezoelectric layer 20 to generate ultrasonic waves, an electric signal should be applied to the piezoelectric member constituting the piezoelectric layer 20. Therefore, the piezoelectric member is provided with electrodes 22 and 23, that is, a ground electrode 22 and a signal electrode 23, to which an electric signal is applied.

When the piezoelectric layer 20 is formed as a one-dimensional array or two-dimensional array, the ground electrode 22 and signal electrode 23 are formed on each of the elements 21 constituting the array.

Also, to apply electric signals to the ground electrode 22 and the signal electrode 23 formed on each of the elements 21, conductive patterns 32 and 33 are formed in each of the grooves 31 in which the elements 21 are installed.

As shown in FIG. 3, the conductive patterns 32 and 33 may be formed to extend from both lateral sides of the groove 31 to outside the groove 31. The portions of the conductive patterns 32 and 33 extending outside the groove 31 may be electrically connected to an electric signal-supply member, for example, a printed circuit board (PCB) or a flexible printed circuit board (FPCB).

The conductive patterns 32 and 33 extending toward each other from any two adjacent grooves 31 to the outside thereof may be formed to have different polarities. When the conductive patterns 32 and 33 are formed in this way, the conductive patterns 32 and 33 extending toward each other from the adjacent grooves 31 to the outside thereof are arranged not to contact each other.

When the conductive patterns 32 and 33 extending toward each other from any two adjacent grooves 31 to the outside thereof have the same polarity, that is, when both conductive patterns 32 and 33 contact the ground electrode 22 or both conductive patterns 32 and 33 contact the signal electrode 23, they may be connected to each other.

However, the electric signals applied to the elements 21 need to be adjusted differently from each other, and thus the conductive patterns 32 and 33 formed by extending toward each other from the adjacent grooves 31 to the outside thereof may be provided with different polarities and arranged not to contact each other, as shown in FIG. 3.

FIG. 4 shows the piezoelectric member provided with the electrodes 22 and 23 adapted to be installed in the grooves 31.

If the conductive patterns 32 and 33 are formed on opposite lateral side surfaces of the groove 31 as shown in FIG. 3, the ground electrode 22 and signal electrode 23 may be formed on corresponding opposite lateral side surfaces of the element 21 as shown in FIG. 4, so that when the element 21 is installed in the groove 31 (see FIG. 5), the ground electrode 22 and signal electrode 23 formed on the element 21 may contact the conductive patterns 32 and 33, respectively. The ground electrode 22 and signal electrode 23 may be formed only on the opposite lateral side surfaces of the element 21, or may further extend therefrom toward the front-side surface or rear-side surface of the element 21.

Figure 13:
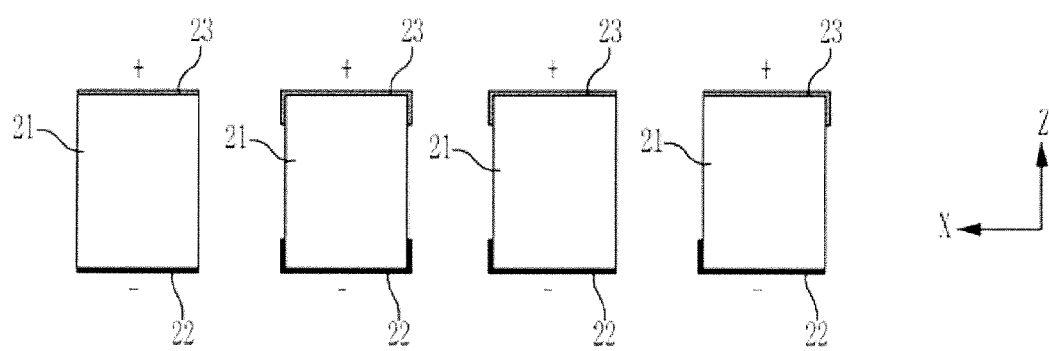
FIG. 13 is a view illustrating a piezoelectric member provided with electrodes to be installed in the grooves of FIGS. 11 and 12.

Alternatively, the ground electrode 22 and signal electrode 23 may be formed on the front-side and rear-side surfaces of the element 21 rather than on the opposite lateral side surfaces of the element 21 as shown in FIG. 13.

FIG. 6 shows the ground electrode 22 and signal electrode 23 formed on the front-side and rear-side surfaces of the element 21 and FIG. 7 illustrates installation of the element 21 of FIG. 6 in the groove 31.

When the ground electrode 22 and signal electrode 23 are formed on the front-side and rear-side surfaces of the element 21, they may extend toward opposite lateral side surfaces so that when the element 21 is installed in the groove 31, the ground electrode 22 and signal electrode 23 formed on the front-side and rear-side surfaces of the element 21, respectively, may contact the corresponding conductive patterns 32 and 33.

Figure 8:
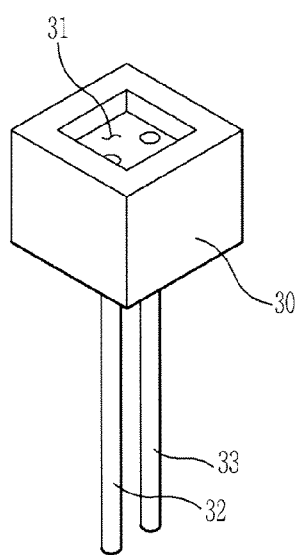
FIG. 8 is a view illustrating another example of formation of conductive patterns in the grooves of the backing layer of the ultrasound probe according to an embodiment of the present disclosure.
Figure 9:
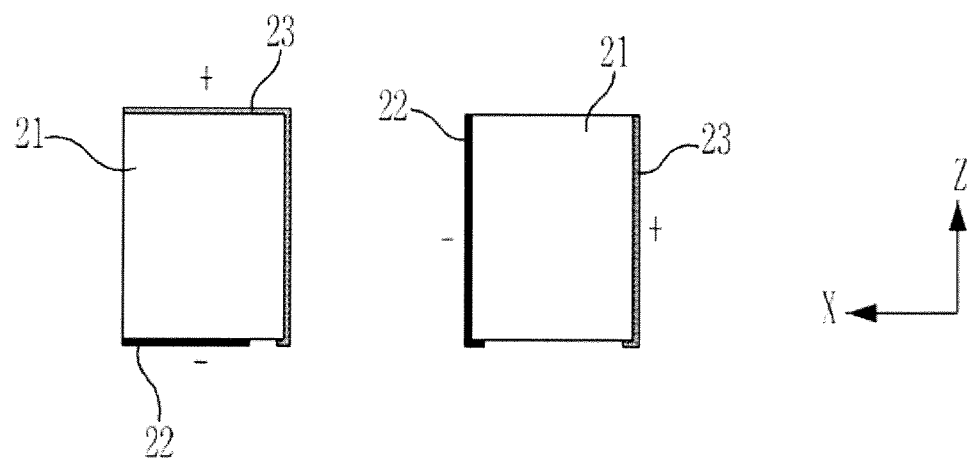
FIG. 9 is a view illustrating a piezoelectric member provided with electrodes to be installed in the grooves of FIG. 8.
Figure 10:
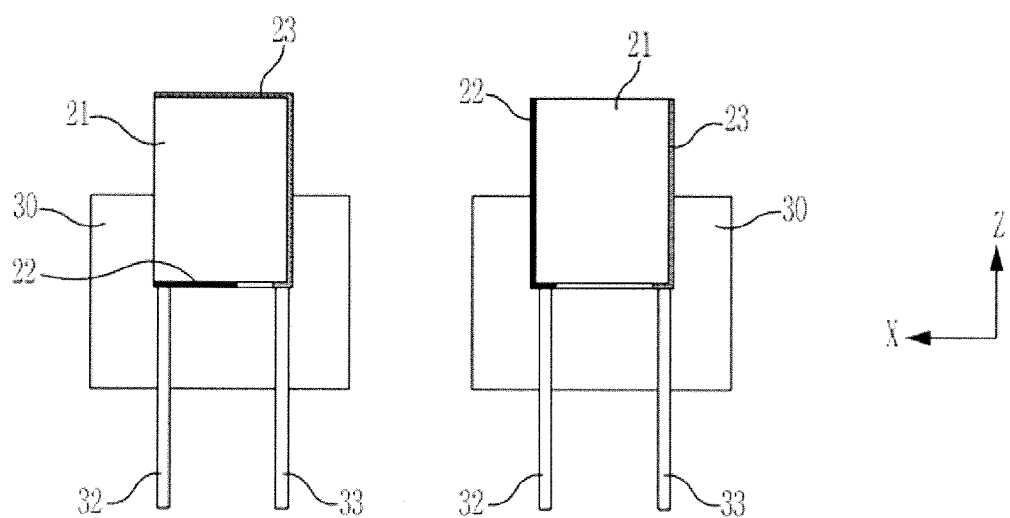
FIG. 10 is a view illustrating installation of the piezoelectric member of FIG. 9 in the grooves of FIG. 8.

FIG. 8 illustrates another example of conductive patterns 32 and 33 formed in the groove 31 of the backing layer 30 of the ultrasound probe according to an exemplary embodiment of the present disclosure, FIG. 9 shows a piezoelectric member that may be installed in the grooves 31 of FIG. 8, and FIG. 10 illustrates installation of the piezoelectric member of FIG. 9 in the grooves 31 of FIG. 8.

As shown in FIG. 8, a bottom of the groove 31 may be provided with two conductive patterns 32 and 33 which are connected respectively to the ground electrode 22 and signal electrode 23. The conductive patterns 32 and 33 may be exposed at the bottom of the groove 31 and extend to a rear side of the backing layer 30 through an internal portion of the backing layer 30. At the rear side of the backing layer 30, the conductive patterns 32 and 33 may be connected to an external member supplying electrical signals.

FIG. 9 shows the piezoelectric member provided with the ground electrode 22 and signal electrode 23 adapted to be installed in the grooves 31.

If the bottom of the groove 31 is provided with two conductive patterns 32 and 33 as shown in FIG. 8, the ground electrode 22 and signal electrode 23 may be formed on the element 21 as shown in FIG. 9, so that when the element 21 is installed in the groove 31 (see FIG. 10), the ground electrode 22 and signal electrode 23 may contact the conductive patterns 32 and 33, respectively.

When the ground electrode 22 and signal electrode 23 are formed on the front-side and rear-side surfaces of the element 21, the ground electrode 22 is arranged on the rear-side surface and the signal electrode 23 on the front-side surface. The signal electrode 23 formed on the front-side surface of the element 21 may be arranged to extend to the rear-side surface of the element 21 along a lateral side surface of the element 21. Alternatively, the ground electrode 22 may be formed on the front-side surface of the element 21 and the signal electrode 23 formed on the rear-side surface of the element 21 as shown in, for example, FIG. 6.

When the ground electrode 22 and signal electrode 23 are formed on lateral side surfaces of the element 21, the ground electrode 22 and the signal electrode 23 may be respectively arranged on the opposite lateral side surfaces of element 21 and both may be arranged to extend to the rear-side surface of the element 21.

As an alternative to forming the ground electrode 22 and signal electrode 23 on the front-side and rear-side surfaces or the opposite lateral side surfaces, one of the ground electrode 22 and signal electrode 23 may extend to a surface of the element 21 on which the other one of the ground electrode 22 and signal electrode 23 is formed, as shown in the example on the left in FIG. 9. Alternatively, both the ground electrode 22 and signal electrode 23 may be formed to extend from the lateral side surfaces of the element 21 to the rear-side surface of the element 21 as shown in the example on the right in FIG. 9, and in this case the conductive patterns 32 and 33 may be provided only at the bottom of the groove 31.

Since the ground electrode 22 and signal electrode 23 extending to the rear-side surface of the element 21 only need to be connected to the respective conductive patterns 32 and 33 formed on the bottom of the groove 31, they may be arranged to occupy as small an area of the rear-side surface of the element 21 as possible.

Figure 11:
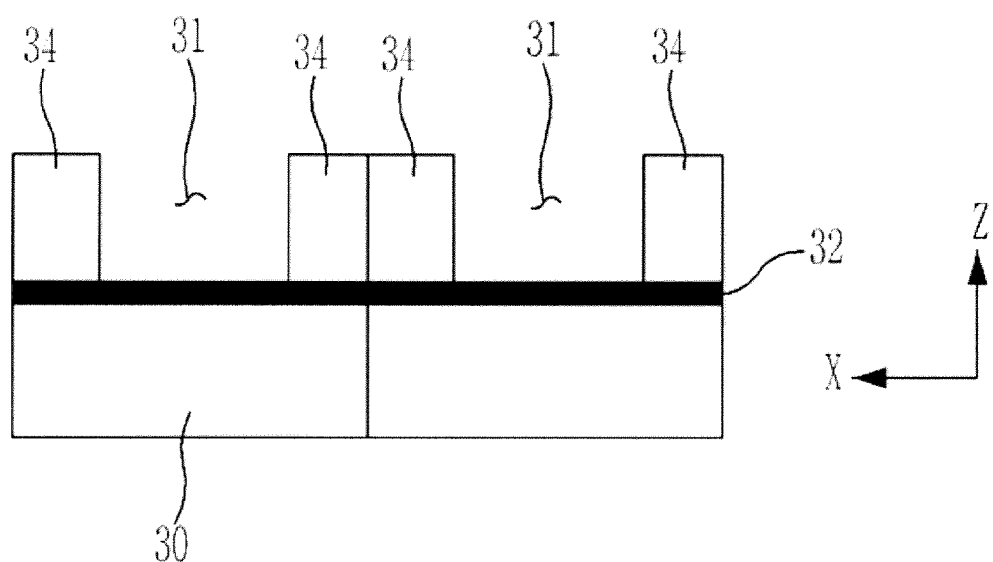
FIGS. 11 and 12 are views illustrating further examples of formation of conductive patterns in the grooves of the backing layer of the ultrasound probe according to an embodiment of the present disclosure.
Figure 12:
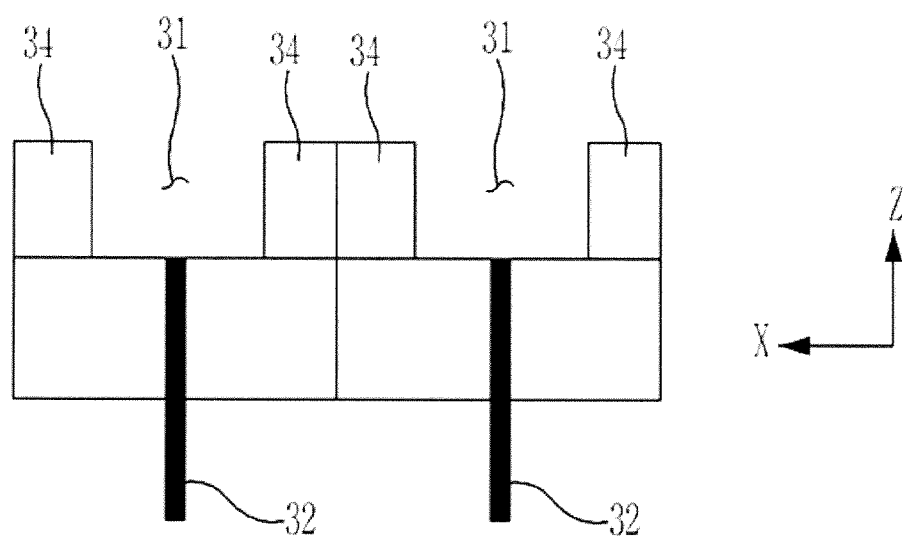

FIGS. 11 and 12 illustrate further examples of conductive patterns formed in the grooves 31 of the backing layer 30 of an ultrasound probe according to another embodiment of the present disclosure, and FIG. 13 shows a piezoelectric member that may be installed in the grooves 31 of FIGS. 11 and 12.

The backing layer 30 shown in FIG. 11 includes a backing member 34 provided with the grooves 31, a backing block 35 to support the backing member 34, and a conductive pattern 32 installed between the backing member 34 and the backing block 35.

The conductive pattern 32 is electrically connected to an external member supplying electric signals and contacts one of the ground electrode 22 and signal electrode 23 of the element 21.

That is, in this exemplary embodiment, there are not two conductive patterns 32 and 33 formed to contact the ground electrode 22 and signal electrode 23, respectively, like the conductive patterns 32 and 33 in FIGS. 3 and 8 described above, but one conductive pattern 32 is provided to contact only one of the ground electrode 22 and signal electrode 23.

The conductive pattern 32 shown in FIG. 12 may be exposed at the bottom of the groove 31 to contact the ground electrode 22 of the element 21 to be installed in the groove 31, and may extend to the rear side of the backing layer 30 through the internal portion (e.g., backing block 35) of the backing layer 30. At the rear side of the backing layer 30, the conductive pattern 32 may be connected to an external member supplying electric signals.

Similar to the conductive pattern 32 in FIG. 11, the conductive pattern 32 in FIG. 12 contacts one of the ground electrode 22 and signal electrode 23 of the element 21.

FIG. 13 illustrates a piezoelectric member provided with the ground electrode 22 and signal electrode 23 to be installed in the grooves 31 in FIGS. 11 and 12.

If one conductive pattern 32 is formed at the bottom of the groove 31 as in FIGS. 11 and 12, the ground electrode 22 and signal electrode 23 formed on the element 21 may be arranged on the front-side and rear-side surfaces of the element 21 as shown in FIG. 13, so that when the element 21 is installed in the groove 31, the one of the ground electrode 22 and signal electrode 23 may contact the conductive pattern 32.

In the illustrated example shown in FIG. 13, among the ground electrode 22 and signal electrode 23, only the ground electrode 22 formed on the rear-side surface of the element 21 may receive an electric signal from the conductive pattern 32 formed in the groove 31.

The signal electrode 23 formed on the front-side surface of the element 21 may receive an electric signal from a separate conductive pattern to be installed on the front-side surface of the piezoelectric member.

The ground electrode 22 and signal electrode 23 may be formed only on the front-side and rear-side surfaces of the element 21, or may be arranged to extend from the front-side and rear-side surfaces to the opposite lateral side surfaces.

Figure 14:
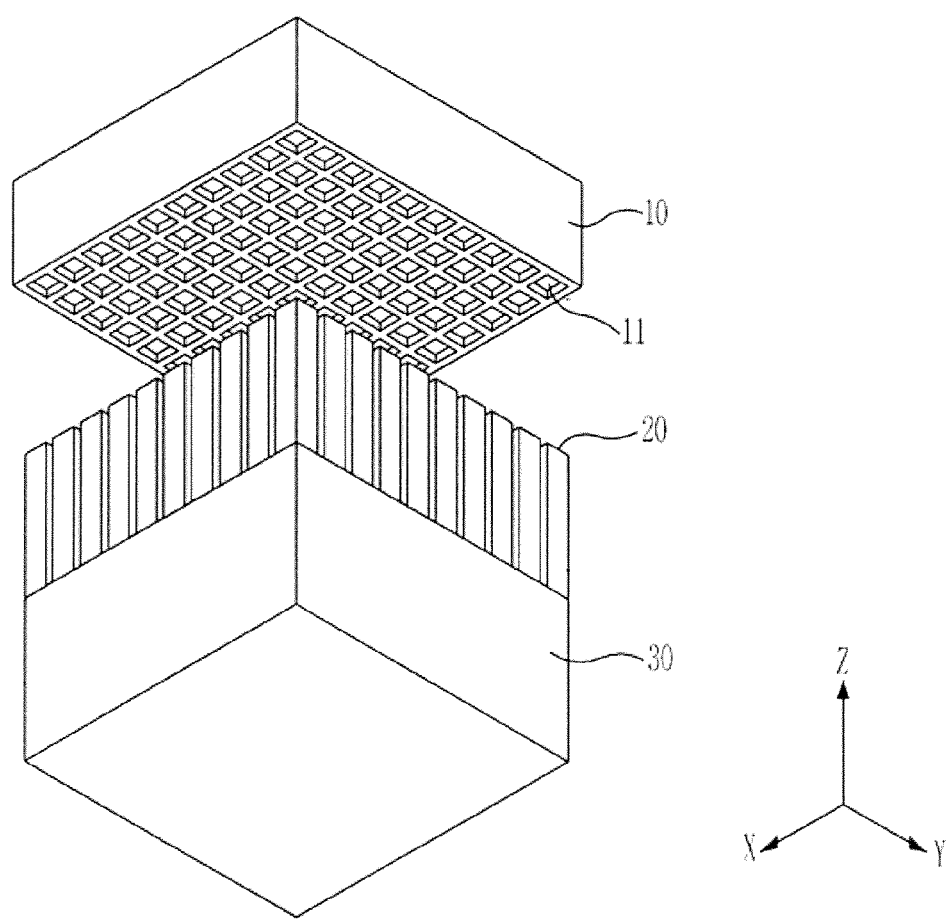
FIGS. 14 and 15 are exploded perspective views illustrating an ultrasound probe according to another embodiment of the present disclosure.
Figure 15:
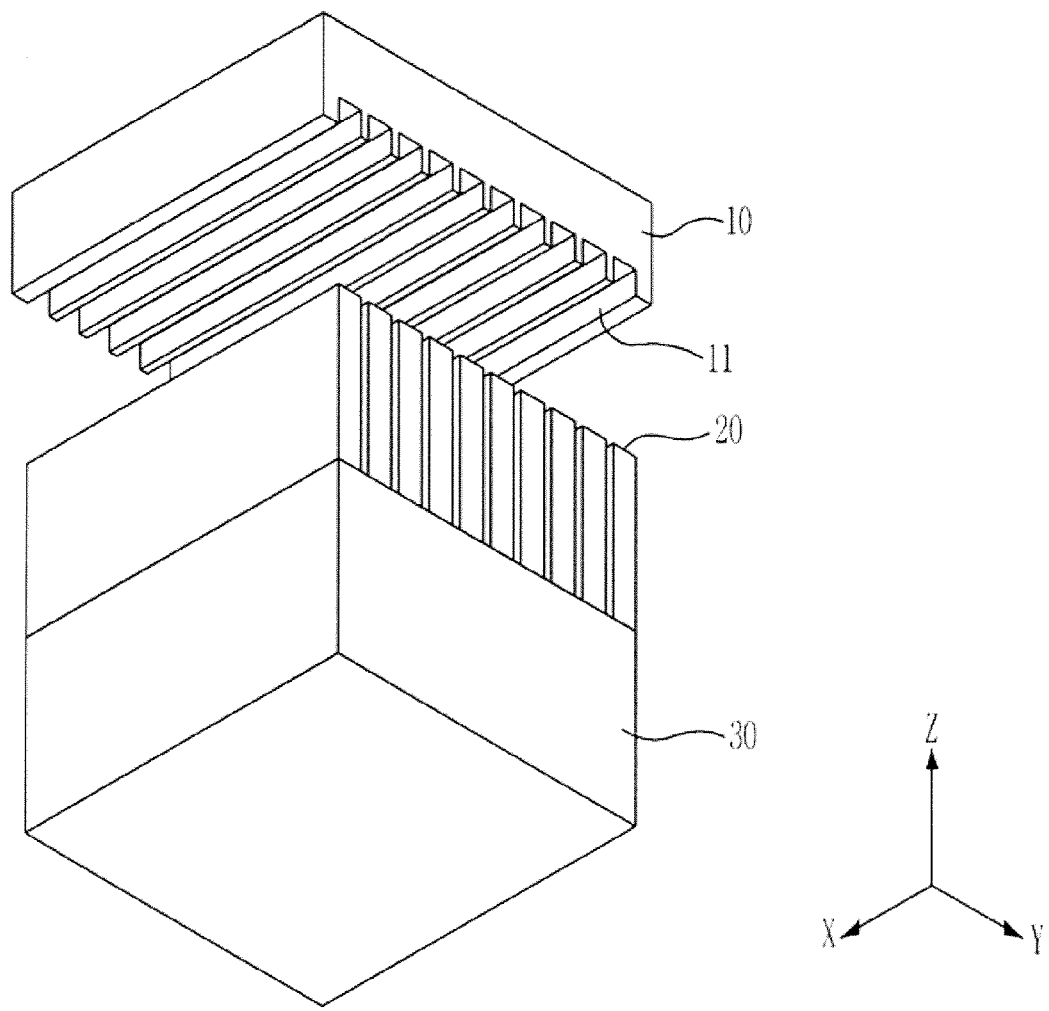

FIGS. 14 and 15 illustrate another exemplary embodiment of the present disclosure. That is, grooves 11 in which corresponding piezoelectric members are installed are formed in the matching layer 10 rather than in the backing layer 30.

If the piezoelectric layer 20 is formed as a two-dimensional array, the matching layer 10 is formed to have a plurality of grooves 11 arranged in a two-dimensional array, as shown in FIG. 14.

The number of grooves 11 may be equal to that of the elements 21 constituting the two-dimensional array of the piezoelectric layer 20, and each of the grooves 31 may be formed to have the same or a similar cross-sectional shape as that of the corresponding element 21 so that the respective elements 21 may be installed in the grooves 31.

If the piezoelectric layer 20 is formed as a one-dimensional array, the matching layer 10 is formed to have a plurality of grooves 11 arranged in a one-dimensional array, as shown in FIG. 15.

The number of grooves 11 may be equal to that of the elements 21 constituting the one-dimensional array of the piezoelectric layer 20, and each of the grooves 31 may be formed to have the same or a similar cross-sectional shape as that of the corresponding element 21 so that the respective elements 21 may be installed in the grooves 31.

The depth of the grooves 11 may be set to allow the elements 21 to be stably seated while not degrading the efficiency of generating ultrasonic waves.

The manufacturing technique used for forming the grooves 11 in the matching layer 10 is not limited. Various manufacturing techniques may be used depending on, for example, the shape of the grooves 11. For instance, in one exemplary process, the matching layer 10 provided with grooves 11 may be manufactured through casting.

If the grooves 11 are formed in the matching layer 10, the orientation of the ground electrode 22 and signal electrode 23 formed on the elements 21 and the conductive patterns 32 and 33 formed in the grooves 11 are opposite to that defined in the exemplary embodiments illustrated in FIGS. 3 to 13. The other details of the ground electrode 22 and signal electrode 23 and the conductive patterns 32 and 33 are the same as those for the embodiments illustrated in FIGS. 3 to 13, and thus for the other details, refer to the description given above with respect to FIGS. 3 to 13.

FIG. 16 is a flowchart illustrating a manufacturing method of the ultrasound probe according to an exemplary embodiment of the present disclosure.

As shown in FIG. 16, the matching layer 10 is installed on one side of the piezoelectric member (100).

After the matching layer 10 is installed on the one side of the piezoelectric member, the piezoelectric member and the matching layer 10 are processed into a one-dimensional or two-dimensional array (110).

The array of the piezoelectric member may be formed through a dicing process. After the piezoelectric member is formed, it may have the shape shown in FIGS. 1 and 2.

Once the piezoelectric member is formed into the array, the ground electrode 22 and signal electrode 23 are formed on each of the elements 21 constituting the array (120), the grooves 31 are provided on one side of the backing layer 30 in the same one-dimensional or two-dimensional array as that of the piezoelectric member (130), and then the conductive patterns 32 and 33 are formed in the grooves 31 (140).

If the piezoelectric member is a one-dimensional array, the grooves 31 to be formed on the backing layer 30 are also manufactured in a one-dimensional array. If the piezoelectric member is a two-dimensional array, the grooves 31 to be formed on the backing layer 30 are also manufactured in a two-dimensional array.

The number of grooves 31 may be equal to that of the elements 21 constituting the array of the piezoelectric member, and each of the grooves 31 is formed to have the same or similar cross-sectional shape as that of the corresponding element 21.

The manufacturing technique used for forming the grooves 31 in the backing layer 30 is not limited. Various manufacturing techniques may be used depending on, for example, the shape of the grooves 31. For instance, in one exemplary process, the backing layer 30 provided with grooves 31 may be manufactured through casting.

The ground electrode 22 and signal electrode 23 are formed on each of the elements 21 constituting the array of the piezoelectric member, and the structure of the ground electrode 22 and signal electrode 23 is related to that of the conductive patterns 32 and 33 installed in the grooves 31 of the backing layer 30.

As shown in FIG. 4, the ground electrode 22 and signal electrode 23 formed on opposite lateral side surfaces of the element 21 may have various shapes. If the ground electrode 22 and signal electrode 23 are formed to extend from the front-side and rear-side surfaces of the element 21 to the opposite lateral side surfaces as shown in FIG. 6, the conductive patterns 32 and 33 may be formed in the groove 31 of the backing layer 30 as shown in FIG. 3 or FIG. 7.

If two conductive patterns are formed at the bottom of the groove 31 as shown in FIG. 8, the ground electrode 22 and signal electrode 23 may be formed on the element 21 as shown in FIG. 9, so that when the element 21 is installed in the groove 31, the ground electrode 22 and signal electrode 23 may contact the conductive patterns 32 and 33, respectively.

That is, when the ground electrode 22 and signal electrode 23 are formed on the front-side and rear-side surfaces of the element 21, the ground electrode 22 is arranged on the rear-side surface and the signal electrode 23 on the front-side surface. The signal electrode 23 formed on the front-side surface of the element 21 may be arranged to extend to the rear-side surface of the element 21 along a lateral side surface of the element 21. Alternatively, the ground electrode 22 may be formed on the front-side surface of the element 21 and the signal electrode 23 formed on the rear-side surface of the element 21.

When the ground electrode 22 and signal electrode 23 are formed on opposite lateral side surfaces of the element 21, the ground electrode 22 and the signal electrode 23 may be respectively arranged on the opposite lateral sides of element 21 and both may be arranged to extend to the rear-side surface of the element 21.

When the ground electrode 22 and signal electrode 23 of various different shapes are formed on the front-side and rear-side surfaces of the element 21 in the manner shown in FIG. 13, the conductive pattern 32 may be formed in the groove 31 of the backing layer 30 as shown in FIG. 11 or FIG. 12. In this case, the signal electrode 23 formed on the front-side surface of the element 21 may receive an electric signal from a separate conductive pattern to be installed on the front-side surface of the piezoelectric member.

After the conductive patterns 32 and 33 are formed in the grooves 31 of the backing layer 30, the array of the piezoelectric member is installed in the grooves 31 of the backing layer 30 (150).

The array of the piezoelectric member should be installed such that the ground electrode 22 and signal electrode 23 formed on the elements 21 of the array contact the conductive patterns 32 and 33, respectively.

When the array of the piezoelectric member is installed in the grooves 31, an adhesive, a silver epoxy, a conductive material, or the like, may be inserted between contact surfaces of the element 21 and the groove 31 for increasing accuracy in arranging the elements 21 to allow the elements 21 to be securely installed in the grooves 31.

FIG. 17 is a flowchart illustrating a manufacturing method of the ultrasound probe according to another exemplary embodiment of the present disclosure.

As shown in FIG. 17, the piezoelectric member is installed on one side of the backing layer (200).

After being installed on one side of the backing layer, the piezoelectric member is processed into a one-dimensional or two-dimensional array (210).

The piezoelectric member may be processed into an array through a dicing process. After the piezoelectric member is processed, it has the shape as shown in FIGS. 14 and 15.

Once the piezoelectric member is formed into the array, the ground electrode 22 and signal electrode 23 are formed on each of the elements 21 constituting the array (220), the grooves 11 are formed on one side of the matching layer 10 in the same one-dimensional or two-dimensional array as that of the piezoelectric member (230), and then the conductive patterns 32 and 33 are formed in the grooves 11 (240).

If the piezoelectric member is a one-dimensional array, the grooves 11 to be formed in the matching layer 10 are also processed in a one-dimensional array. If the piezoelectric member is a two-dimensional array, the grooves 11 to be formed are also processed in a two-dimensional array. The number of grooves 11 may be equal to that of the elements 21 constituting the array of the piezoelectric member, and each of the grooves 11 is formed to have the same or similar cross-sectional shape as that of the corresponding element 21.

The manufacturing technique used for forming the grooves 11 in the matching layer 10 is not limited. Various manufacturing techniques may be used depending on, for example, the shape of the grooves 11. For instance, in one exemplary process, the matching layer 10 provided with the grooves 11 may be manufactured through casting.

If the grooves 11 are formed in the matching layer 10, the orientation of the ground electrode 22 and signal electrode 23 formed on the elements 21 and the conductive patterns 32 and 33 formed in the grooves 11 are opposite to that for the case in which the grooves 31 are formed in the backing layer 30. The other details of the ground electrode 22 and signal electrode 23 and the conductive patterns 32 and 33 are the same as those for the case in which the grooves 31 are formed in the backing layer 30, and thus for the other details, refer to the description given above with respect to FIG. 16.

Once the conductive patterns 32 and 33 are formed in the grooves 11 of the matching layer 10, the array of the piezoelectric member is installed in the grooves 11 of the matching layer 10 (250).

When the array of the piezoelectric member is installed in the grooves 11, an adhesive, a silver epoxy, a conductive material, or the like, may be inserted between contact surfaces of the element 21 and the groove 11 for increasing accuracy in arranging the elements 21 to allow the elements 21 to be securely installed in the grooves 11.

As is apparent from the above description, an ultrasound probe and manufacturing method thereof according to exemplary embodiments of the present disclosure may lower a defect rate and increase yield of ultrasound probes by improving the way the components of the ultrasound probe are connected to each other.

In addition, the ultrasound probe and manufacturing method thereof according to exemplary embodiments of the present disclosure may reduce cross-talk and provide a wider bandwidth and good sensitivity.

Further, as the grooves can be formed in the matching layer, convenient and various designs may be allowed.

Although a few embodiments of the present disclosure have been shown and described, it would be appreciated by those having ordinary skill in the art that changes may be made in these embodiments without departing from the principles and spirit of the disclosure, the scope of which is defined in the claims and their equivalents.

What is claimed is:

1. An ultrasound probe comprising:
a piezoelectric array including one or more elements; and
a backing layer disposed on a rear-side surface of the piezoelectric array and including, on a front-side surface of the backing layer, at least one groove having two opposing sides, wherein each element of the one or more elements included in the piezoelectric array is installed in one of the at least one groove,
wherein at least a first surface of each element includes a ground electrode,
at least a second surface of each element, including a surface opposite to the first surface, includes a signal electrode,
the at least one groove includes one or more conductive patterns extending from each of the two opposing sides of the groove to outside the groove, and
each of the conductive patterns is connected to at least one of the ground electrode and the signal electrode.

2. The ultrasound probe according to claim 1, wherein:
the piezoelectric array is arranged as one of a one-dimensional array and a two-dimensional array, and
the at least one groove has a shape corresponding to the piezoelectric array.

3. An ultrasound probe comprising:
a piezoelectric array including one or more elements; and
a matching layer disposed on a front-side surface of the piezoelectric array and including, on a rear-side surface of the matching layer, at least one groove having two opposing sides, wherein each element of the one or more elements included in the piezoelectric array is installed in one of the at least one groove,
wherein at least a first surface of each element includes a ground electrode,
at least a second surface of each element, including an opposite surface of the first surface, includes a signal electrode,
the at least one groove includes one or more conductive patterns which extend from each of the opposing sides of the groove to outside the groove, and
each of the conductive patterns is connected to at least one of the ground electrode and the signal electrode.

4. The ultrasound probe according to claim 3, wherein:
the piezoelectric array is arranged as one of a one-dimensional array and a two-dimensional array; and
the at least one groove has a shape corresponding to the piezoelectric array.

5. The ultrasound probe according to claim 3, wherein each of the conductive patterns is electrically connected to the at least one of the ground electrode and the signal electrode to apply an electric signal to the one or more elements.

6. A manufacturing method of an ultrasound probe comprising:
forming at least one groove, having two opposing sides, on one side of a backing layer;
forming one or more conductive patterns which extend from each of the two opposing sides of the groove to outside the groove,
forming a ground electrode on at least a first surface of each of elements constituting an array of a piezoelectric member;
forming a signal electrode on at least a second surface of each of the elements, including a surface opposite to the first surface; and
installing, in the at least one groove, the array of the piezoelectric member provided with the ground and signal electrodes,
wherein the installing the array of the piezoelectric member comprises:
installing the array so that each of the conductive patterns is connected to at least one of the ground electrode and the signal electrode.

7. The manufacturing method according to claim 6, wherein the forming at least one groove comprises:
arranging, on the one side of the backing layer, the at least one groove in one of a one-dimensional array and a two-dimensional array.

8. The manufacturing method according to claim 6, wherein the installing the array of the piezoelectric member further comprises:
installing a matching layer on one side of the piezoelectric member;
processing the piezoelectric member on which the matching layer is installed into one of a one-dimensional array and a two-dimensional array.

9. The manufacturing method according to claim 8, wherein the forming the one or more conductive patterns comprises:
forming the one or more conductive patterns to apply an electric signal to the processed piezoelectric member.

10. A manufacturing method of an ultrasound probe comprising:
forming at least one groove, having two opposing sides, on one side of a matching layer;
forming one or more conductive patterns which extend from each of the two opposing sides of the groove to outside the groove,
forming a ground electrode on at least a first surface of each of elements constituting an array of a piezoelectric member;
forming a signal electrode on at least a second surface of each of the elements, including a surface opposite to the first surface; and
installing, in the at least one groove, the array of the piezoelectric member provided with the ground and signal electrodes,
wherein the installing the array of the piezoelectric member comprises:
installing the array so that each of the conductive patterns is connected to at least one of the ground electrode and the signal electrode.

11. The manufacturing method according to claim 10, wherein the forming at least one groove comprises:
arranging, on the one side of the matching layer, the at least one groove in one of a one-dimensional array and a two-dimensional array.

12. The manufacturing method according to claim 10, wherein the installing the array of the piezoelectric member further comprises:
processing the piezoelectric member into one of a one-dimensional array and a two-dimensional array.

13. The manufacturing method according to claim 12, wherein the forming the one or more conductive patterns comprises:
forming the one or more conductive patterns to apply an electric signal to the processed piezoelectric member.

14. An ultrasound probe comprising:
a piezoelectric array including one or more elements, piezoelectric array having opposing front-side and rear-side surfaces;
a backing layer disposed on the rear-side surface for absorbing at least a portion of ultrasonic waves generated in the piezoelectric array; and
a matching layer disposed on the front-side surface for reducing a difference in acoustic impedance between the piezoelectric array and a subject,
wherein at least one of the backing layer and matching layer includes at least one groove having two opposing sides,
each element of the one or more elements included in the piezoelectric array is installed in one of the at least one groove,
at least a first surface of the each element includes a ground electrode,
at least a second surface, including a surface opposite to the first surface, includes a signal electrode,
the at least one groove includes one or more conductive patterns which extend from each of the two opposing sides of the groove to outside the groove, and
each of the conductive patterns is connected to at least one of the ground electrode and the signal electrode.

15. The ultrasound probe of claim 14, wherein the backing layer includes the at least one groove.

16. The ultrasound probe of claim 14, wherein the matching layer includes the at least one groove.

17. The ultrasound probe of claim 14, wherein the one or more conductive patterns are configured to apply an electric signal to the piezoelectric array.

18. The ultrasound probe of claim 1, wherein at least one of the conductive patterns is connected to the ground electrode, and at least another of the conductive patterns is connected to the signal electrode.

19. The ultrasound probe of claim 1, wherein at least one of the conductive patterns has a different polarity than at least another of the conductive patterns.

20. The ultrasound probe of claim 3, wherein at least one of the conductive patterns is connected to the ground electrode, and at least another of the conductive patterns is connected to the signal electrode.

21. The ultrasound probe of claim 3, wherein at least one of the conductive patterns has a different polarity than at least another of the conductive patterns.

22. The method of claim 6, wherein at least one of the conductive patterns is connected to the ground electrode, and at least another of the conductive patterns is connected to the signal electrode.

23. The method of claim 6, wherein at least one of the conductive patterns has a different polarity than at least another of the conductive patterns.

24. The method of claim 10, wherein at least one of the conductive patterns is connected to the ground electrode, and at least another of the conductive patterns is connected to the signal electrode.

25. The method of claim 10, wherein at least one of the conductive patterns has a different polarity than at least another of the conductive patterns.

26. The ultrasound probe of claim 14, wherein at least one of the conductive patterns is connected to the ground electrode, and at least another of the conductive patterns is connected to the signal electrode.

27. The ultrasound probe of claim 14, wherein at least one of the conductive patterns has a different polarity than at least another of the conductive patterns.

* * * * *